US00PP35011P2

(12) United States Plant Patent
Takahashi et al.

(10) Patent No.: US PP35,011 P2
(45) Date of Patent: Feb. 28, 2023

(54) ***GENTIAN* PLANT NAMED 'ASHIRO 29-2030'**

(50) Latin Name: ***Gentiana* L. hybrid**
Varietal Denomination: Ashiro 29-2030

(71) Applicant: HACHIMANTAI CITY, Hachimantai (JP)

(72) Inventors: Ryo Takahashi, Hachimantai (JP); Yutaro Takamura, Morioka (JP); Rina Suzuki, Hachimantai (JP); Takashi Hikage, Morioka (JP)

(73) Assignee: HACHIMANTAI CITY, Hachimantai (JP)

( * ) Notice: Subject to any disclaimer, the term of this patent is extended or adjusted under 35 U.S.C. 154(b) by 0 days.

(21) Appl. No.: 17/556,621

(22) Filed: Dec. 20, 2021

(51) Int. Cl.
*A01H 5/02* (2018.01)
*A01H 6/40* (2018.01)

(52) U.S. Cl.
USPC ..... Plt./433

(58) Field of Classification Search
USPC ..... Plt./433
CPC ... A01H 5/02; A01H 5/00; A01H 6/40; A01H 6/00
See application file for complete search history.

*Primary Examiner* — June Hwu
(74) *Attorney, Agent, or Firm* — Seckel IP, PLLC

(57) ABSTRACT

A new variety of *Gentiana* L. plant (Japanese gentian) which has a color of inner side of lobes which is strong purplish blue (96C on RHS Colour Chart) and a time of flowering in mid-October.

4 Drawing Sheets

Botanical classification: *Gentiana* L. hybrid.
Variety denomination: 'Ashiro 29-2030'.

BACKGROUND OF THE NEW VARIETY

The present invention relates to a new and distinct variety of Japanese gentian, *Gentiana* L., which has been given the variety denomination 'Ashiro 29-2030'.

This new gentian has a color of inner side of lobes which is strong purplish blue (96C on RHS Colour Chart) and a time of flowering in mid-October. It is adapted for use as cut flowers or pot flowers.

ORIGIN OF THE VARIETY

The variety resulted from a multiple-step cross-breeding program starting from a group of unpatented varieties. The ancestor varieties were unpatented strains owned by the applicant, having the company-internal names: '17INP' which belongs to the species *Gentiana triflora*, and '26-904', '12-316-3', '17SUP', and '8-130SP6A1', which belong to the species *Gentiana scabra*. Group crosses and/or self-crosses with a single individual were performed. The program had seven steps, as shown in the map of FIG. 6, which also indicates the company-internal names of the intermediary, unpatented strains. At each step, the individuals with good plant and flower shape were selected. The corresponding species identification is ((*scabra*x*triflora*)x*scabra*))x((*scabra*x*triflora*)x*scabra*)).

The multiple-step cross-breeding program was performed over multiple growing seasons up to 2018; in October 2018, selection of the variety was performed. We asexually reproduced the variety by vegetative reproduction through cuttings, tissue culturing via lateral bud culture, and in October 2020, the new variety was found to be stable and asexually reproduced true to type in successive generations.

The variety was developed and propagated in Iwate, Japan.

The variety can be propagated by cutting (optimal timing is mid-February) and/or tissue culturing via lateral bud culture.

Cultivation of the variety does not require particular conditions. Maintenance and storage method of the plant material can be by tissue culture via lateral bud culture.

The variety is adapted for use as cut flowers or pot flowers.

SUMMARY OF THE VARIETY

The variety is distinguished by the color of inner side of lobes being strong purplish blue (96C on RHS Colour Chart) and by its time of flowering in mid-October, as compared to 'Shine Blue Ashiro' variety whose color of inner side of lobes is strong blue (N95A on the RHS Colour Chart) and whose time of flowering in late September. 'Shine Blue Ashiro' is unpatented.

A comparison with Shine Blue Ashiro variety is presented as follows in Table 1:

TABLE 1

| | Shine Blue Ashiro | Ashiro 29-2030 |
|---|---|---|
| Color of inner side of lobes | Strong blue (N95A on the RHS Colour Chart) | strong purplish blue (96C on the RHS Colour Chart) |
| Time of flowering | Late September | mid-October |

Additional distinguishing characteristics of the 'Ashiro 29-2030' plant are the five (5.0 on average) lobes of the paracorolla, and the strong purplish-blue color (96D on R.H.S. Colour Chart), with spots, of the secondary lobes with acute apex in-between the main lobes of the corolla.

BRIEF DESCRIPTION OF THE DRAWINGS

In the accompanying drawings, which are as nearly true as is reasonable possible to make in a color illustration of this type.

Figure 1:
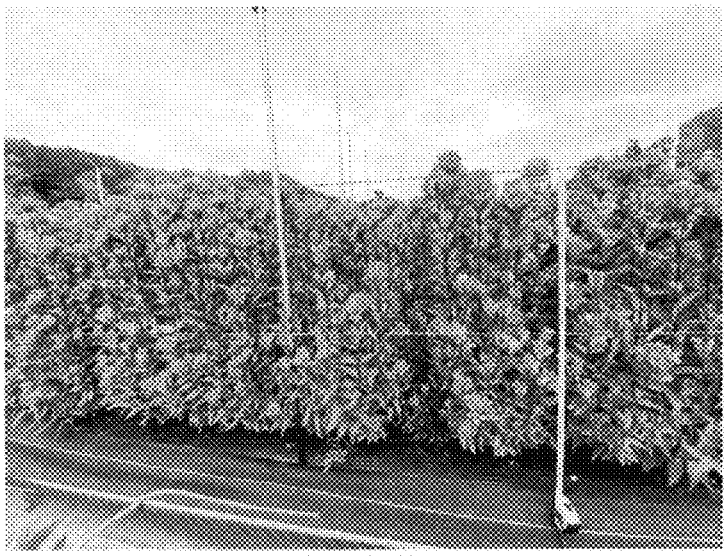
FIG. 1 is a color photograph showing the 'Ashiro 29-2030' plant as grown in a culturing bed.
Figure 2:
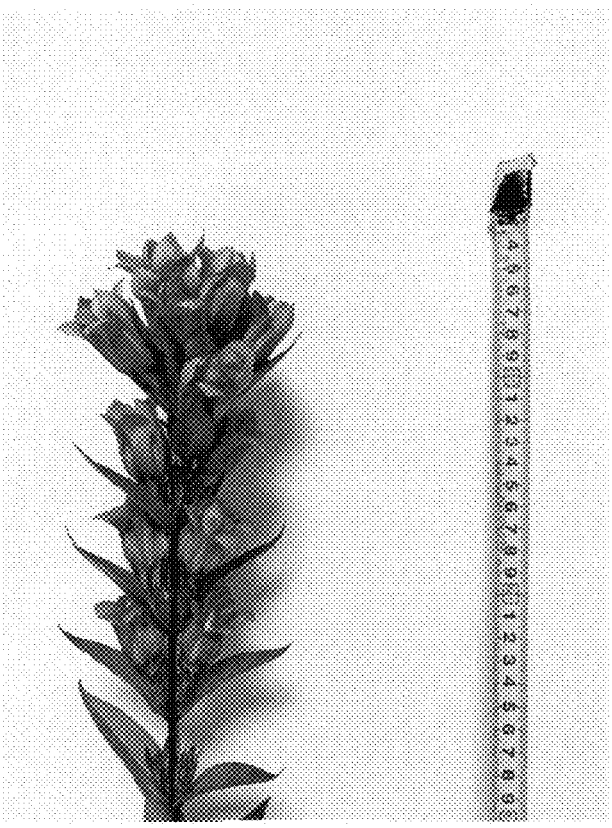
FIG. 2 is a color photograph showing flowers of the 'Ashiro 29-2030' plant.
Figure 3:
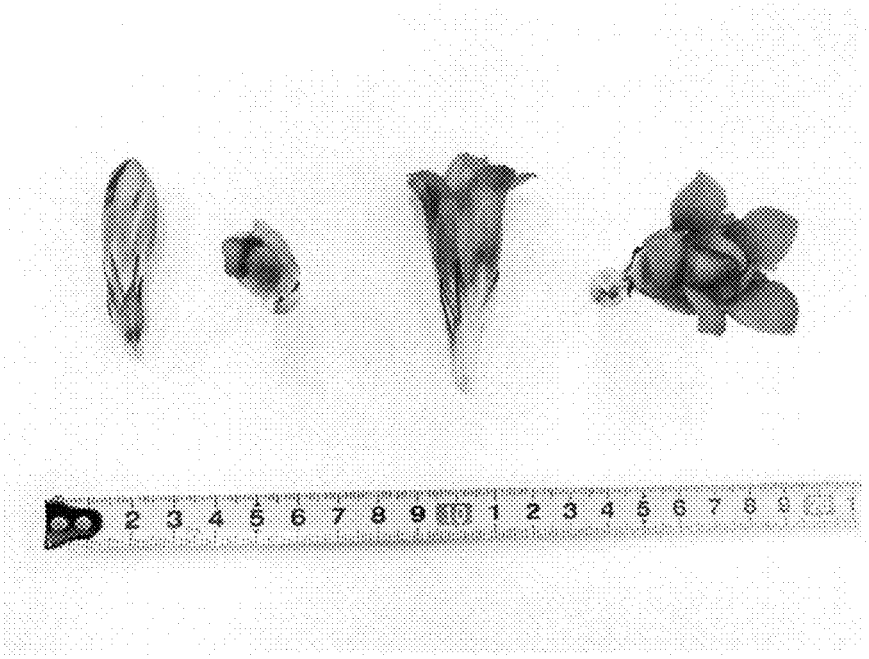
FIG. 3 is a color photograph showing flowering stages of flowers of the 'Ashiro 29-2030' plant.
Figure 4:
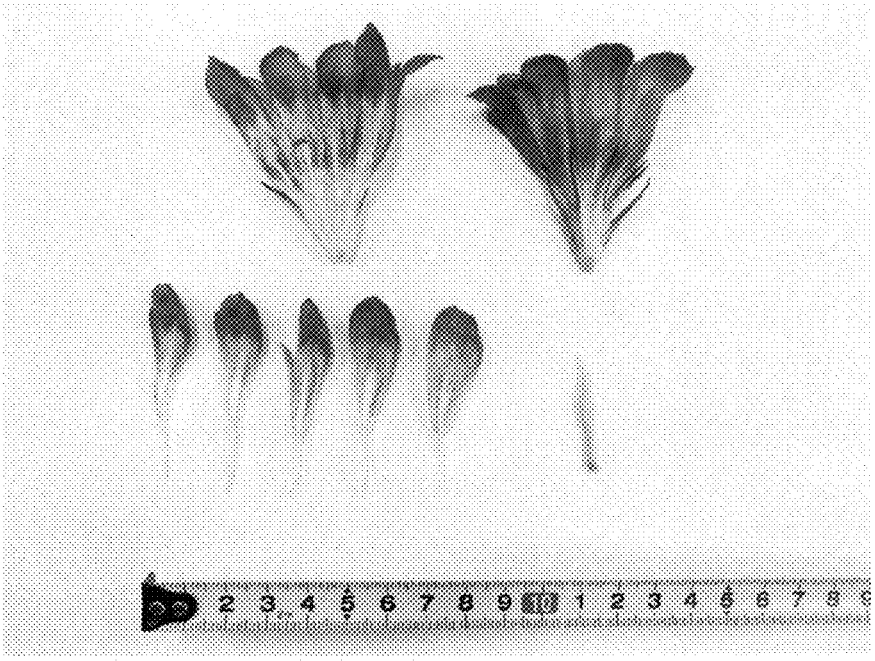
FIG. 4 is a color photograph showing petals of flowers of the 'Ashiro 29-2030' plant.
Figure 5:
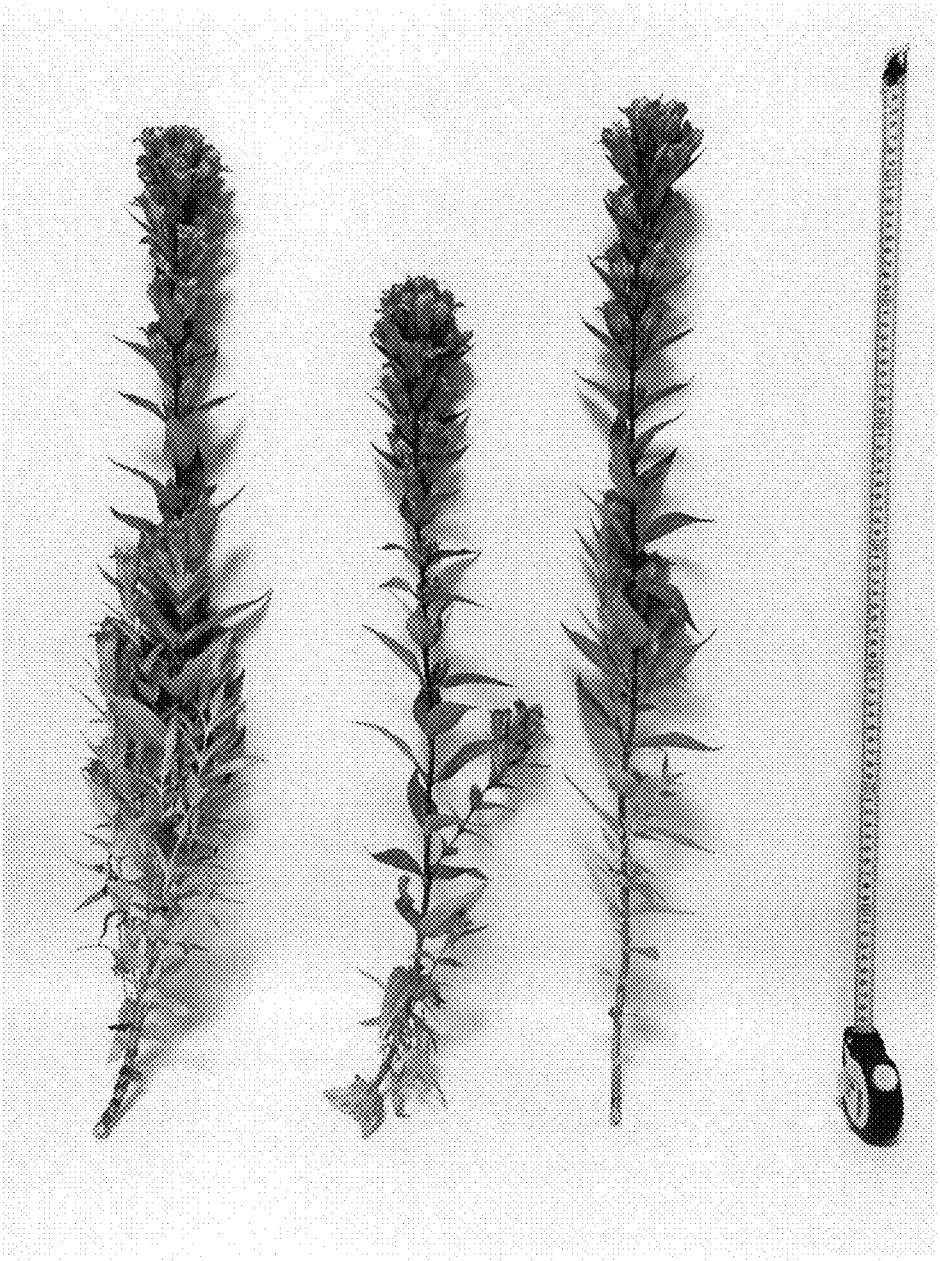
FIG. 5 is another color photograph showing flowers of the 'Ashiro 29-2030' plant.
Figure 6:
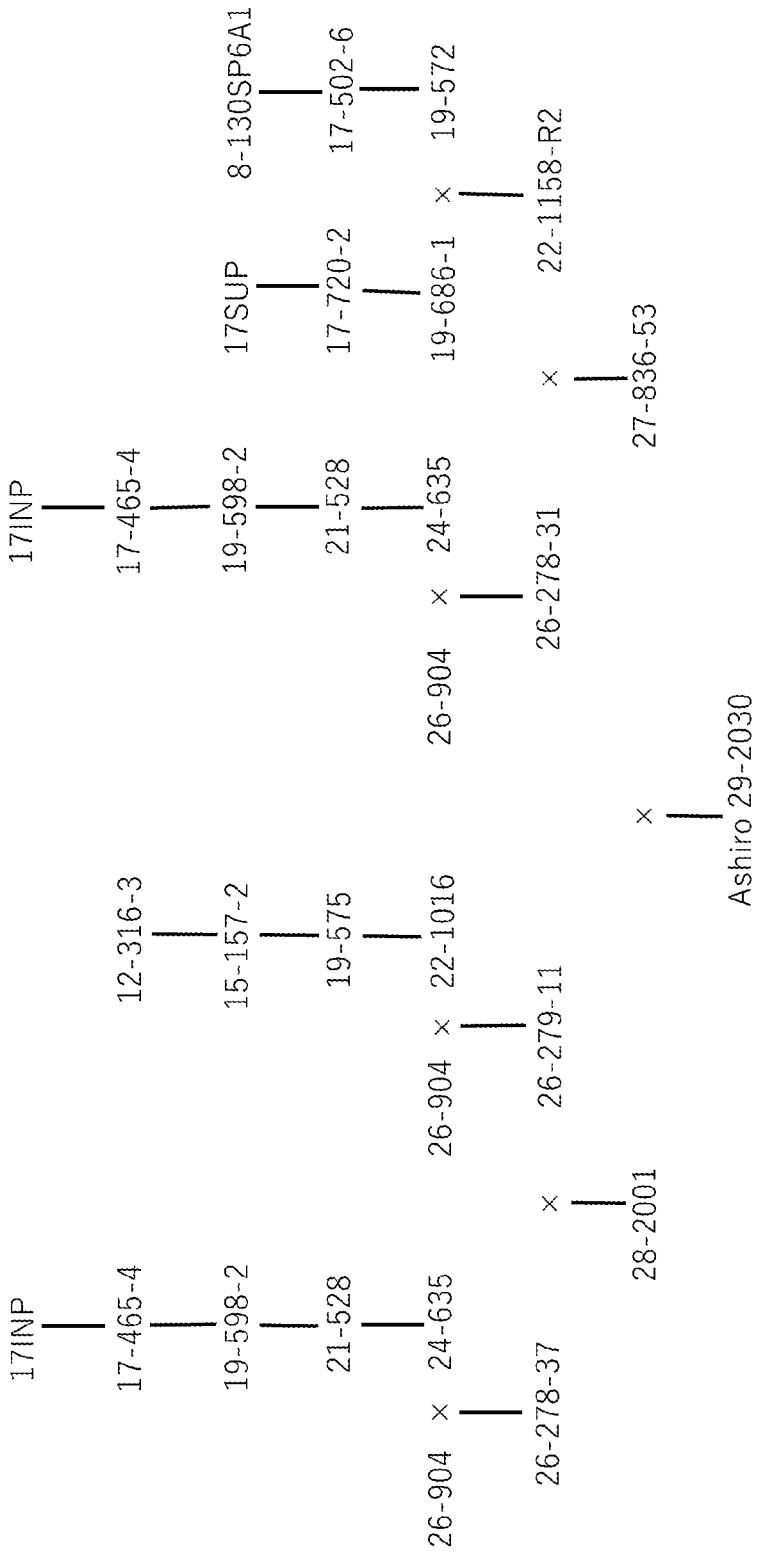
FIG. 6 is a map showing the steps of the cross-breeding program from which the variety was obtained.

Due to chemical and/or digital development, processing and printing, the plants or portions of plants depicted in the photographs may or may not be precisely accurate, when compared to the actual botanical specimens.

DETAILED DESCRIPTION OF THE INVENTION

The plants in the botanical description below and shown in the Figures were grown in Iwate, Japan. The plants were collected in October 2020 at age 16 months.

Colors are given according to The 2015 R.H.S. Colour Chart.

Botanical description:

TABLE 2

| | | |
|---|---|---|
| Stem | Length: | 82.7 cm |
| | Stem shape in cross-section: | circular |
| | Thickness (main flowering stem): | 4.1 mm |
| | Number of flowering stems per plant (average): | 14.9 |
| | Texture: | smooth |
| | Color: | strong yellow green (145A on RHS Colour Chart) |
| | Anthocyanin coloration at two thirds from base: | present |
| | Number of internodes longer than 5 mm (average): | 22.7 |
| | Length of internode in central third: | 4.0 cm |
| | Side shoots: | present |
| | Number of side shoots with only one node (average): | 1.5 |
| | Number of side shoots with more than one node (average): | 7.5 |
| | Position of longest leaf: | in lower third |
| Leaf | Length: | 7.8 cm |
| | Leaf arrangement: | opposite leaf arrangement |
| | Leaf attachment: | sessile |
| | Leaf apex: | acuminate |
| | Leaf margin: | entire |
| | Leaf base: | acute |
| | Leaf texture (inner side): | smooth |
| | Leaf texture (outer side): | smooth |
| | Leaf color (inner side): | strong yellow green (143A on RHS Colour Chart) |
| | Leaf color (outer side): | moderate yellow green (139D on RHS Colour Chart) |

TABLE 2-continued

| | | |
|---|---|---|
| | Leaf venation pattern: | parallel venation (three lines) |
| | Width: | 5.0 cm |
| | Shape: | narrow lanceolate |
| | Shape in cross section: | folded upwards |
| | Shape in longitudinal section: | straight |
| | Twisting: | absent |
| | Number of conspicuous veins: | 3 |
| | Anthocyanin coloration: | absent |
| Inflorescence | Distribution of flowers: | clustered |
| | Position of flowers: | terminal and axillary |
| Plant: | Number of terminal flowers (average): | 7.5 |
| | Typical plant height: | about 82.7 cm (cut flower or potted plant) |
| | Typical growth habit: | erect |
| | Plant spread (average): | 49.7 cm |
| | Sequence of flowering: | from top downwards |
| | Number of flowers at central flowering node (average): | 2.9 |
| | Number of flowering node: | 5.7 |
| Flower bud (about 3 days before flowering) | Shape of bud: | narrow oval |
| | Length of bud (average): | 46.01 mm |
| | Diameter of bud (average): | 9.79 mm |
| | Color of bud: | greyish purplish red (N77D on RHS Colour Chart) |
| Flower | Type: | double |
| | Time of flowering: | mid-October |
| | Flower longevity (potted plant): | 13 days |
| | Flower longevity (cut flower): | 7 days |
| Corolla | Depth: | 54.5 mm |
| | Diameter at middle third: | 17.7 mm |
| | Shape: | campanulate |
| | Diameter at top: | 32.3 mm |
| | Curvature of lobes: | reflexed |
| | Color of inner side of lobes: | strong purplish blue (96C on RHS Colour Chart) |
| | Tube length (average): | 31.4 mm |
| | Color of upper part of inner side of tube: | strong purplish blue (96C on RHS Colour Chart) |
| | Color of upper part of outer side of tube: | greyish purplish red (N77D on RHS Colour Chart) |
| | Streaked pattern on outer side of tube: | present |
| | Color of streaked pattern on outer side of tube: | greyish purplish red (N77D on RHS Colour Chart) |
| | Density of spots on the inner side of the corolla lobes: | sparse |
| | Density of spots on the upper part of the inner side of the corolla tube: | sparse |
| | Density of spots on the outer side of the corolla tube: | absent |
| | Number of lobes: | 5 |
| | Length of lobes: | 11.0 mm |
| | Width of lobes: | 11.3 mm |
| | Shape of lobes: | ovate |
| | Shape of distal end of lobes: | acute |
| | Presence of secondary lobes: | present |
| | Average number of secondary lobes per flower: | 5 |
| | Shape of secondary lobe apex: | acute |
| | Color of secondary lobes: | strong purplish-blue (96D on RHS Colour Chart) for both surfaces |
| | Presence of spots on secondary lobes: | present |

TABLE 2-continued

| | | |
|---|---|---|
| Paracorolla | Presence of paracorolla: | present |
| | Number of paracorolla lobes (average): | 5.0 |
| | Paracolla apex shape: | acute |
| Calyx | Anthocyanin coloration: | present |
| | Length of tube: | 16.7 mm |
| | Diameter of tube: | 6.6 mm |
| | Shape of tube: | funnel-shaped |
| | Shape of lobe: | narrow lanceolate |
| Sepal | Sepal number: | 5 |
| | Sepal lobe shape: | narrow lanceolate |
| | Sepal apex: | acute |
| | Sepal color (inner side): | strong yellow green (141D on the RHS Colour Chart) |
| | Sepal color (outer side): | moderate yellow green (138B on the RHS Colour Chart) |
| Reproductive organs | Stamens and anther: | stamens are mutated into petals |
| | Time of flowering: | late October |
| | Pistil number: | 1 |
| | Pistil length (average): | 36.0 mm |
| | Anther shape: | narrow oval |
| | Anther color: | light yellow green (145D on RHS Colour Chart) |

In the above chart, specific numbers correspond to average values.

Other features of the plant are as follows:

*Disease resistance.*—Normal resistance was observed for pests and diseases in Iwate, Japan, using pest control by chemical spraying for gentian.

*Cold hardiness.*—Strong, the variety can withstand winter in Iwate, Japan, including low temperatures of about −10° C. with abundant snow.

*Heat tolerance.*—Normal, the variety can withstand summer in Iwate, Japan, including high temperatures of about 35° C.

*Flower fragrance.*—Absent.

We claim:

1. A new and distinct variety of *Gentiana* plant named 'Ashiro 29-2030', substantially as described and illustrated herein.

* * * * *